United States Patent
Dieing et al.

(10) Patent No.: US 6,964,774 B1
(45) Date of Patent: *Nov. 15, 2005

(54) FORMULATIONS OF HAIR COSMETICS

(75) Inventors: Reinhold Dieing, Schifferstadt (DE); Michael Gotsche, Aachen (DE); Peter Hössel, Schifferstadt (DE); Axel Sanner, Frankenthal (DE); Alfred Leinenbach, Gönnheim (DE); Keith Leslie Rutherford, Wirral (GB)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/913,980

(22) PCT Filed: Feb. 10, 2000

(86) PCT No.: PCT/EP00/01070

§ 371 (c)(1),
(2), (4) Date: Aug. 21, 2001

(87) PCT Pub. No.: WO00/49998

PCT Pub. Date: Aug. 31, 2000

(30) Foreign Application Priority Data

Feb. 22, 1999 (DE) ................................ 199 07 587

(51) Int. Cl.$^7$ ............................. A61K 6/00; A61K 7/00; A61K 7/42; C08F 283/06; C08F 218/08

(52) U.S. Cl. ......................... 424/401; 424/47; 424/59; 525/451; 525/71; 525/531

(58) Field of Search ............................ 424/401, 47, 59; 525/451, 71, 531

(56) References Cited

U.S. PATENT DOCUMENTS

| | | |
|---|---|---|
| 3,946,749 A | 3/1976 | Papantoniou |
| 4,876,083 A | 10/1989 | Grollier et al. |
| 4,880,618 A | 11/1989 | Grollier et al. |
| 6,403,074 B1 * | 6/2002 | Blankenburg et al. ... 424/70.12 |

FOREIGN PATENT DOCUMENTS

| | | | |
|---|---|---|---|
| WO | 99/04750 | | 2/1999 |
| WO | WO 99/04750 | * | 2/1999 |

* cited by examiner

Primary Examiner—Shaojia Anna Jiang
(74) Attorney, Agent, or Firm—Novak Druce & Quigg

(57) ABSTRACT

The use of polymers obtainable by free-radical polymerization of
 a) at least one vinyl ester of $C_1$–$C_{24}$-carboxylic acids in the presence of
 b) polyether-containing compounds and
 c) optionally one or more other copolymerizable monomers
and subsequent at least partial hydrolysis of the ester functions of the original monomers a), in hair cosmetic formulations.

26 Claims, No Drawings

FORMULATIONS OF HAIR COSMETICS

This application is a 371 of PCT/EP00/01070 filed Feb. 10, 2000 which claims foreign priority to Germany 199 07 587.5 under 35 U.S.C. 119(a)–(d), filed Feb. 22, 1999.

The present invention relates to aqueous or aqueous/alcoholic hair cosmetic formulations comprising, as film former, polymers prepared by polymerization of vinyl esters and optionally other free-radically copolymerizable monomers in the presence of a polyether-containing compound, and subsequent at least partial hydrolysis.

Synthetic polymers have been used for setting hairstyles for almost 50 years. Whereas initially preference was given to using vinyllactam homo- and copolymers, polymers containing carboxylate groups became more important later on. Requirements for hair-setting resins are, for example, strong hold at atmospheric humidity, elasticity, wash-off from the hair, and compatibility with other formulation components. The combination of different properties creates problems. For example, polymers with good setting properties often exhibit low elasticity, hence when the hairstyle is subjected to mechanical stress, the setting action is often considerably impaired as a result of damage to the polymer film.

There is therefore a need for improvement in particular in producing elastic hairstyles which have strong hold, even at high atmospheric humidity, and good wash-off while the feel of the hair is good.

It is an object of the present invention to find hair cosmetic formulations containing film-forming polymers which impart strong hold and also high elasticity to the hairstyle.

We have found that this object is achieved according to the invention using polymers obtainable by free-radical polymerization of
a) at least one vinyl ester in the presence of
b) polyether-containing compounds and optionally at least one other copolymerizable monomer c) and subsequent at least partial hydrolysis of the ester functions of the original monomers a), in hair cosmetic formulations.

Graft polymers of polyvinyl alcohol on polyalkylene glycols are already known.

DE 1 077 430 describes a process for the preparation of graft polymers of vinyl esters on polyalkylene glycols.

DE 1 094 457 and DE 1 081 229 describe processes for the preparation of graft polymers of polyvinyl alcohol on polyalkylene glycols by hydrolysis of the vinyl esters and their use as protective colloids, water-soluble packaging films, as sizes and finishes for textiles and in cosmetics.

In the preparation of the polymers used according to the invention, grafting onto the polyether-containing compounds (b) can result during the polymerization, which can lead to the advantageous properties of the polymers. However, mechanisms other than grafting are also conceivable.

Depending on the degree of grafting, the polymers used according to the invention are taken to mean pure graft polymers and also mixtures of the abovementioned graft polymers with nongrafted polyether-containing compounds and homo- or copolymers of the monomers a) and c).

Polyether-containing compounds (b) which can be used are either polyalkylene oxides, based on ethylene oxide, propylene oxide, butylene oxide and other alkylene oxides, or polyglycerol. Depending on the type of monomer units, the polymers contain the following structural units.

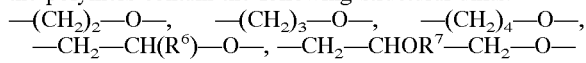

where
$R^6$ is $C_1$–$C_{24}$-alkyl;
$R^7$ is hydrogen, $C_1$–$C_{24}$-alkyl, $R^6$—C(=O)—, $R^6$—NH—C(=O)—.

The structural units can either be homopolymers or random copolymers and block copolymers.

As polyether (b), preference is given to using polymers of the formula I,

in which the variables independently of one another have the following meanings:
$R^1$ is hydrogen, $C_1$–$C_{24}$-alkyl, $R^6$—C(=O)—, $R^6$—NH—C(=O)—, polyalcohol radicals;
$R^5$ is hydrogen, $C_1$–$C_{24}$-alkyl, $R^6$—C(=O)—, $R^6$—NH—C(=O)—;
$R^2$ to $R^4$ are —(CH$_2$)$_2$—, —(CH$_2$)$_3$—, —(CH$_2$)$_4$—, —CH$_2$—CH(R$^6$)—, —CH$_2$—CHOR$^7$—CH$_2$—;
$R^6$ is $C_1$–$C_{24}$-alkyl;
$R^7$ is hydrogen, $C_1$–$C_{24}$-alkyl, $R^6$—C(=O)—, $R^6$—NH—C(=O)—;
A is —C(=O)—O, —C(=O)—B—C(=O)—O, —C(=O)—NH—B—NH—C(=O)—O;
B is —(CH$_2$)$_t$—, arylene, optionally substituted;
n is from 1 to 1000;
s is from 0 to 1000;
t is from 1 to 12;
u is from 1 to 5000;
v is from 0 to 5000;
w is from 0 to 5000;
x is from 0 to 5000;
y is from 0 to 5000;
z is from 0 to 5000.

The terminal primary hydroxyl groups of the polyethers prepared on the basis of polyalkylene oxides, and the secondary OH-groups of polyglycerol can in this connection either be present in free unprotected form, or be etherified with alcohols of chain length $C_1$–$C_{24}$ or esterified with carboxylic acids of chain length $C_1$–$C_{24}$, or reacted with isocyanates to give urethanes.

Alkyl radicals which may be mentioned for $R^1$ and $R^5$ to $R^7$ are branched or unbranched $C_1$–$C_{24}$-alkyl chains, preferably methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, 2-ethylhexyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl or n-eicosyl.

Preferred representatives of the abovementioned alkyl radicals which may be mentioned are branched or unbranched $C_1$–$C_{12}$-, particularly preferably $C_1$–$C_6$-alkyl chains.

The molecular weight of the polyethers is less than 1000000 (number average), preferably in the range from 300 to 100000, particularly preferably in the range from 500 to 50000, very particularly preferably in the range from 800 to 40000.

Homopolymers of ethylene oxide or copolymers carrying an ethylene oxide content of from 40 to 99% by weight are advantageously used. For the ethylene oxide polymers to be used in preference, the content of copolymerized ethylene oxide is thus from 40 to 100 mol %. Suitable comonomers for these copolymers are propylene oxide, butylene oxide and/or isobutylene oxide. Suitable examples are copolymers of ethylene oxide and propylene oxide, copolymers of ethylene oxide and butylene oxide, and copolymers of ethylene oxide, propylene oxide and at least one butylene oxide. The ethylene oxide content of the copolymers is preferably from 40 to 99 mol %, the propylene oxide content is from 1 to 60 mol % and the content of butylene oxide in the copolymers is from 1 to 30 mol %. As well as straight-chain homo- or copolymers, it is also possible to use branched homo- or copolymers as polyether-containing compounds b).

Branched polymers can be prepared by adding ethylene oxide and optionally also propylene oxide and/or butylene oxides to, for example, polyalcohol radicals, e.g. to pentaerythritol, glycerol, or to sugar alcohols such as D-sorbitol and D-mannitol, but also to polysaccharides such as cellulose and starch. The alkylene oxide units can be randomly distributed or be in the form of blocks within the polymer.

It is, however, also possible to use polyesters of polyalkylene oxides and aliphatic or aromatic dicarboxylic acids, e.g. oxalic acid, succinic acid, adipic acid and terephthalic acid having molar masses of from 1500 to 25000, as described, for example, in EP-A-0 743 962, as polyether-containing compound. In addition, it is also possible to use polycarbonates by reaction of polyalkylene oxides with phosgene or carbonates such as, for example, diphenyl carbonate, and polyurethanes by reaction of polyalkylene oxides with aliphatic and aromatic diisocyanates.

Particularly preferred polyethers (b) are polymers of the formula I having an average molecular weight of from 300 to 100000 (number average), in which the variables independently of one another have the following meanings:
$R^1$ is hydrogen, $C_1$–$C_{12}$-alkyl, $R^6$—C(=O)—, $R^6$—NH—C(=O)—, polyalcohol radical;
$R^5$ is hydrogen, $C_1$–$C_{12}$-alkyl, $R^6$—C(=O)—, $R^6$—NH—C(=O)—;
$R^2$ to $R^4$ are —(CH$_2$)$_2$—, —(CH$_2$)$_3$—, —(CH$_2$)$_4$—, —CH$_2$—CH($R^6$)—, —CH$_2$—CHO$R^7$—CH$_2$—;
$R^6$ is $C_1$–$C_{12}$-alkyl;
$R^7$ is hydrogen, $C_1$–$C_{12}$-alkyl, $R^6$—C(=O)—, $R^6$—NH—C(=O)—;
n is from 1 to 8;
s is 0;
u is from 2 to 2000;
v is from 0 to 2000;
w is from 0 to 2000.

Very particularly preferred polyethers b) are polymers of the formula I having an average molecular weight of from 500 to 50000 (number average), in which the variables independently of one another have the following meanings:
$R^1$ is hydrogen, $C_1$–$C_6$-lkyl, $R^6$—C(=O)—, $R^6$—NH—C(=O)—;
$R^5$ is hydrogen, $C_1$–$C_6$-alkyl, $R^6$—C(=O)—, $R^6$—NH—C(=O)—;
$R^2$ to $R^4$ are —(CH$_2$)$_2$—, —(CH$_2$)$_3$—, —(CH$_2$)$_4$—, —CH$_2$—CH($R^6$)—, —CH$_2$—CHO$R^7$—CH$_2$—;
$R^6$ is $C_1$–$C_6$-alkyl;
$R^7$ is hydrogen, $C_1$–$C_6$-alkyl, $R^6$—C(=O)—, $R^6$—NH—C(=O)—;
n is 1;
s is 0;
u is from 5 to 500;
v is from 0 to 500;
w is from 0 to 500.

However, the polyethers used may also be Silicone derivatives. Suitable silicone derivatives are the compounds known under the INCI name dimethicone copolyols or silicone surfactants, such as, for example, those available under the tradenames Abil® (T. Goldschmidt), Alkasil® (Rhône-Poulenc), Silicone Polyol Copolymer® (Genesee), Belsil® (Wacker), Silwet® (Witco, Greenwich, Conn., USA) or Dow Corning (Dow Corning). These include compounds having the CAS numbers 64365-23-7; 68937-54-2; 68938-54-5; 68937-55-3.

Silicones are generally used in hair cosmetics to improve the feel. The use of polyether-containing silicone derivatives as polyether (b) in the polymers according to the invention can therefore additionally lead to an improvement in the feel of the hair.

Preferred representatives of those polyether-containing silicone derivatives are those which contain the following structural elements:

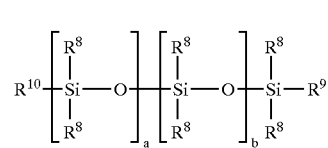

where:

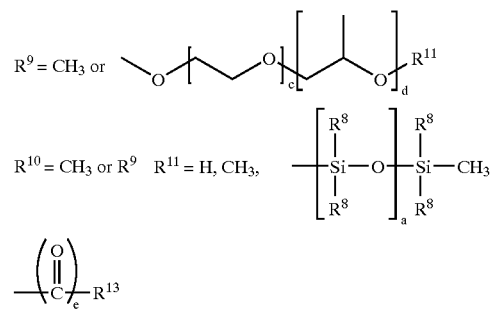

$R^{13}$ is a $C_1$–$C_{40}$ organic radical which can contain amino, carboxyl or sulfonate groups, or where e=0, is also the anion of an inorganic acid, and where the radicals $R^8$ can be identical or different, and come either from the group of aliphatic hydrocarbons having from 1 to 20 carbon atoms, are cyclic aliphatic hydrocarbons having from 3 to 20 carbon atoms, are of an aromatic nature or are identical to $R^{12}$, where:

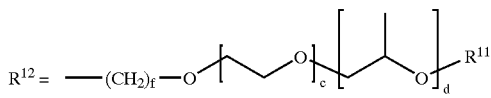

with the proviso that at least one of the radicals $R^8$, $R^9$ or $R^{10}$ is a polyalkylene oxide-containing radical as defined above, and f is an integer from 1 to 6, a and b are integers such that the molecular weight of the polysiloxane block is between 300 and 30000, c and d can be integers between 0 and 50, with the proviso that the sum c+d is greater than 0, and e is 0 or 1.

Preferred radicals $R^9$ and $R^{12}$ are those in which the sum c+d is between 5 and 30.

The groups $R^8$ are preferably chosen from the following group: methyl, ethyl, propyl, butyl, isobutyl, pentyl, isopentyl, hexyl, octyl, decyl, dodecyl and octadecyl, cycloaliphatic radicals, specifically cyclohexyl, aromatic groups, specifically phenyl or naphthyl, mixed aromatic-aliphatic radicals such as benzyl or phenyl ethyl and tolyl and xylyl and $R^{12}$.

Particularly suitable radicals $R^{11}$ are those in which where $R^{11} = -(CO)_e-R^{13}$ $R^{13}$ is any desired alkyl, cycloalkyl or aryl radical which has between 1 and 40 carbon atoms and which can carry other ionogenic groups such as $NH_2$, COOH, $SO_3H$.

Preferred inorganic radicals $R^{13}$ are, where e=0, phosphate and sulfate.

Particularly preferred polyether-containing silicone derivatives are those of the structure:

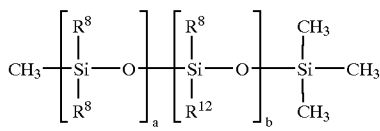

In addition, homo- and copolymers of polyalkylene oxide-containing ethylenically unsaturated monomers, such as, for example, polyalkylene oxide (meth)acrylates, polyalkylene oxide vinyl ethers, polyalkylene oxide (meth)acrylamides, polyalkylene oxide allylamides or polyalkylene oxide vinylamides can also be used as polyether (b). It is of course also possible to use copolymers of such monomers with other ethylenically unsaturated monomers.

It is, however, also possible to use reaction products of polyethyleneimines with alkylene oxides as polyether-containing compounds b). In this case, the alkylene oxides used are preferably ethylene oxide, propylene oxide, butylene oxide and mixtures thereof, particularly preferably ethylene oxide. Polyethyleneimines which can be used are polymers having number-average molecular weights of from 300 to 20000, preferably from 500 to 10000, very particularly preferably from 500 to 5000. The weight ratio between used alkylene oxide and polyethyleneimine is in the range from 100:1 to 0.1:1, preferably in the range from 50:1 to 0.5:1, very particularly preferably in the range from 20:1 to 0.5:1.

For the polymerization in the presence of the polyethers b), the following free-radically polymerizable monomers may be mentioned as component a):

Vinyl esters of aliphatic, saturated or unsaturated $C_1-C_{24}$ carboxylic acids, such as, for example, formic acid, acetic acid, propionic acid, butyric acid, valeric acid, isovaleric acid, caproic acid, caprylic acid, capric acid, undecylenic acid, lauric acid, myristic acid, palmitic acid, palmitoleic acid, stearic acid, oleic acid, arachidic acid, behenic acid, lignoceric acid, cerotinic acid and melissic acid.

Preference is given to using vinyl esters of the above-mentioned $C_1-C_{1-12}$ carboxylic acids, in particular of $C_1-C_6$ carboxylic acids. Vinyl acetate is very particularly preferred.

It is, of course, also possible to copolymerize mixtures of the respective monomers from group a).

The vinyl esters (a) can in addition also be used in admixture with one or more ethylenically unsaturated copolymerizable comonomers (c), where the content of these additional monomers should be limited to a maximum of 50% by weight. Preference is given to contents of from 0 to 20% by weight. The term ethylenically unsaturated means that the monomers have at least one free-radically polymerizable carbon—carbon double bond which can be mono-, di-, tri- or tetrasubstituted.

The preferred ethylenically unsaturated comonomers (c) additionally used can be described by the following formula:

where

X is chosen from the group of radicals —OH, —OM, —OR$^{16}$, $NH_2$, —NHR$^{16}$, N(R$^{16}$)$_2$;

M is a cation chosen from the group consisting of: $Na^+$, $K^+$, $Mg^{++}$, $Ca^{++}$, $Zn^{++}$, $NH_4^+$, alkyl ammonium, dialkylammonium, trialkylammonium and tetraalkylammonium.

The radicals $R^{16}$ can be identical or different and chosen from the group consisting of —H, $C_1-C_{40}$ linear or branched alkyl radicals, N,N-dimethylaminoethyl, 2-hydroxyethyl, 2-methoxyethyl, 2-ethoxyethyl, hydroxypropyl, methoxypropyl or ethoxypropyl.

$R^{15}$ and $R^{14}$ are independently of one another chosen from the group consisting of: —H, $C_1-C_8$ linear or branched alkyl chains, methoxy, ethoxy, 2-hydroxyethoxy, 2-methoxyethoxy and 2-ethoxyethyl.

Representative but non-limiting examples of suitable monomers (c) are, for example, acrylic acid or methacrylic acid and salts, esters and amides thereof. The salts can be derived from any desired nontoxic metal, ammonium or substituted ammonium counterions.

The esters can be derived from $C_1-C_{40}$ linear, $C_3-C_{40}$ branched or $C_3-C_{40}$ carbocyclic alcohols, from polyfunctional alcohols having from 2 to about 8 hydroxyl groups, such as ethylene glycol, hexylene glycol, glycerol and 1,2,6-hexanetriol, from aminoalcohols or alcohol ethers such as methoxyethanol and ethoxyethanol, (alkyl)polyethylene glycols, (alkyl)polypropylene glycols or ethoxylated fatty alcohols, for example $c_{12}-C_{24}$-fatty alcohols reacted with 1 to 200 ethylene oxide units.

Also suitable are N,N-dialkylaminoalkyl acrylates and methacrylates and N-dialkylaminoalkylacryl- and -methacrylamides of the formula (III)

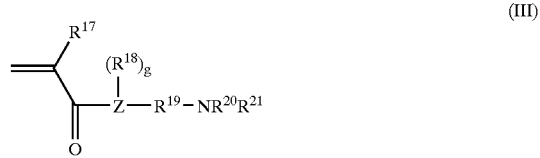

where
$R^{17}$=H, alkyl having from 1 to 8 carbon atoms,
$R^{18}$=H, methyl,
$R^{19}$=alkylene having from 1 to 24 carbon atoms, optionally substituted by alkyl,
$R^{20}$, $R^{21}$=$C_1$–$C_{40}$ alkyl radical,
z=nitrogen when g=1, or oxygen when g=0.

The amides can be unsubstituted, N-alkyl- or N-alkylamino-monosubstituted or N,N-dialkyl-substituted or N,N-dialkylamino-disubstituted, where the alkyl or alkylamino groups are derived from $C_1$–$C_{40}$ linear, $C_3$–$C_{40}$ branched, or $C_3$–$C_{40}$ carbocyclic units. In addition, the alkylamino groups can be quaternized.

Preferred comonomers of the formula III are N,N-dimethylaminomethyl (meth)acrylate, N,N-diethylaminomethyl (meth)acrylate, N,N-dimethylaminoethyl (meth)acrylate, N,N-diethylaminoethyl (meth)acrylate, N-[3-(dimethylamino)propyl]methacrylamide and N-[3-(dimethylamino)propyl]acrylamide.

Comonomers (c) which can likewise be used are substituted acrylic acids and salts, esters and amides thereof, where the substituents on the carbon atoms are in the two or three position of the acrylic acid, and are independently of one another chosen from the group consisting of $C_1$–$C_4$-alkyl, —CN, COOH particularly preferably methacrylic acid, ethacrylic acid and 3-cyanoacrylic acid. These salts, esters and amides of these substituted acrylic acids can be chosen as described above for the salts, esters and amides of acrylic acid.

Other suitable comonomers (c) are allyl esters of $C_1$–$C_{40}$ linear, $C_3$–$C_{40}$ branched or $C_3$–$C_{40}$ carbocyclic carboxylic acids, vinyl or allyl halides, preferably vinyl chloride and allyl chloride, vinyl ethers, preferably methyl, ethyl, butyl or dodecyl vinyl ether, vinylformamide, vinylmethylacetamide, vinylamine; vinyllactams, preferably vinylpyrrolidone and vinylcaprolactam, vinyl- or allyl-substituted heterocyclic compounds, preferably vinylpyridine, vinyloxazoline and allylpyridine.

Also suitable are N-vinylimidazoles of the formula IV, in which $R^{22}$ to $R^{24}$ independently of one another are hydrogen, $C_1$–$C_4$-alkyl or phenyl:

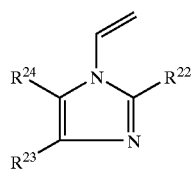

(IV)

Other suitable comonomers (c) are diallylamines of the formula (V)

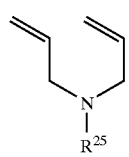

(V)

where $R^{25}$=$C_1$- to $C_{24}$-alkyl

Other suitable comonomers (c) are vinylidene chloride; and hydrocarbons having at least one carbon—carbon double bond, preferably styrene, alpha-methylstyrene, tert-butylstyrene, butadiene, isoprene, cyclohexadiene, ethylene, propylene, 1-butene, 2-butene, isobutylene, vinyltoluene, and mixtures of these monomers.

Particularly suitable comonomers (c) are acrylic acid, methacrylic acid, ethyl acrylic acid, methyl acrylate, ethyl acrylate, propyl acrylate, n-butyl acrylate, iso-butyl acrylate, t-butyl acrylate, 2-ethylhexyl acrylate, decyl acrylate, methyl methacrylate, ethyl methacrylate, propyl methacrylate, n-butyl methacrylate, isobutyl methacrylate, t-butyl methacrylate, 2-ethylhexyl methacrylate, decyl methacrylate, methyl ethacrylate, ethyl ethacrylate, n-butyl ethacrylate, isobutyl ethacrylate, t-butyl ethacrylate, 2-ethylhexyl ethacrylate, decyl ethacrylate, stearyl (meth)acrylate, 2,3-dihydroxypropyl acrylate, 2,3-dihydroxypropyl methacrylate, 2-hydroxyethyl acrylate, hydroxypropyl acrylates, 2-hydroxyethyl methacrylate, 2-hydroxyethyl ethacrylate, 2-methoxyethyl acrylate, 2-methoxyethyl methacrylate, 2-methoxyethyl ethacrylate, 2-ethoxyethyl methacrylate, 2-ethoxyethyl ethacrylate, hydroxypropyl methacrylates, glyceryl monoacrylate, glyceryl monomethacrylate, polyalkylene glycol (meth)acrylates, unsaturated sulfonic acids such as, for example, acrylamidopropane sulfonic acid; acrylamide, methacrylamide, ethacrylamide, N-methylacrylamide, N,N-dimethylacrylamide, N-ethylacrylamide, N-isopropylacrylamide, N-butylacrylamide, N-t-butylacrylamide, N-octylacrylamide, N-t-octylacrylamide, N-octadecylacrylamide, N-phenylacrylamide, N-methylmethacrylamide, N-ethylmethacrylamide, N-dodecylmethacrylamide, 1-vinylimidazole, 1-vinyl-2-methylvinylimidazole, N,N-dimethylaminomethyl (meth)acrylate, N,N-diethylaminomethyl (meth)acrylate, N,N-dimethylaminoethyl (meth)acrylate, N,N-diethylaminoethyl (meth)acrylate, N,N-dimethylaminobutyl (meth)acrylate, N,N-diethylaminobutyl (meth)acrylate, N,N-dimethylaminohexyl (meth)acrylate, N,N-dimethylaminooctyl (meth)acrylate, N,N-dimethylaminododecyl (meth)acrylate, N-[3-(dimethylamino)propyl]methacrylamide, N-[3-(dimethylamino)propyl]acrylamide, N-[3-(dimethylamino)butyl]methacrylamide, N-[8-(dimethylamino)octyl]methacrylamide, N-[12-(dimethylamino)dodecyl]methacrylamide, N-[3-(diethylamino)propyl]methacrylamide, N-[3-(diethylamino)propyl]acrylamide; maleic acid, fumaric acid, maleic anhydride and its half-esters, crotonic acid, itaconic acid, diallyldimethylammonium chloride, vinyl ethers (for example: methyl, ethyl, butyl or dodecyl vinyl ether), vinyl formamide, vinylmethylacetamide, vinylamine; methyl vinyl ketone, maleimide, vinylpyridine, vinylimidazole, vinylfuran, styrene, styrene sulfonate, allyl alcohol, and mixtures thereof.

Of these, particular preference is given to acrylic acid, methacrylic acid, maleic acid, fumaric acid, crotonic acid, maleic anhydride and its half-esters, methyl acrylate, methyl methacrylate, ethyl acrylate, ethyl methacrylate, n-butyl acrylate, n-butyl methacrylate, t-butyl acrylate, t-butyl methacrylate, isobutyl acrylate, isobutyl methacrylate, 2-ethylhexyl acrylate, stearyl acrylate, stearyl methacrylate, N-t-butylacrylamide, N-octylacrylamide, 2-hydroxyethyl acrylate, hydroxypropyl acrylate, 2-hydroxyethyl methacrylate, hydroxypropyl methacrylate, alkylene glycol (meth)acrylates, styrene, unsaturated sulfonic acids such as, for example, acrylamidopropane sulfonic acid, vinylpyrrolidone, vinylcaprolactam, vinyl ethers (e.g.: methyl, ethyl, butyl or dodecyl vinyl ether), vinylformamide, vinylmethylacetamide, vinylamine, 1-vinylimidazole, 1-vinyl-2-methylimidazole, N,N-dimethylaminomethyl methacrylate and N-[3-(dimethylamino)propyl]methacrylamide; 3-methyl-1- vinylimidazolium chloride, 3-methyl-1-vinylimidazolium methylsulfate, N,N-dimethylaminoethyl methacrylate, N-[3-(dimethylamino)propyl]methacrylamide quaternized with methyl chloride, methyl sulfate or diethyl sulfate.

Monomers having one basic nitrogen atom can be quaternized in the following manner:

Suitable for quaternizing the amines are, for example, alkyl halides having from 1 to 24 carbon atoms in the alkyl group, e.g. methyl chloride, methyl bromide, methyl iodide, ethyl chloride, ethyl bromide, propyl chloride, hexyl chloride, dodecyl chloride, lauryl chloride and benzyl halides, in particular benzyl chloride and benzyl bromide. Other suitable quaternizing agents are dialkyl sulfates, in particular dimethyl sulfate or diethyl sulfate. The quaternization of the basic amines can also be carried out with alkylene oxides such as ethylene oxide or propylene oxide in the presence of acids. Preferred quaternizing agents are: methyl chloride, dimethyl sulfate or diethyl sulfate.

The quaternization can be carried out before the polymerization or after the polymerization.

In addition, it is possible to use the reaction products of unsaturated acids, such as, for example, acrylic acid or methacrylic acid, with a quaternized epichlorohydrin of the formula (VI) ($R^{26}=C_1$- to $C_{40}$-alkyl).

(VI)

Examples thereof are, for example: (meth)acryloyloxyhydroxypropyltrimethylammonium chloride and (meth)acryloyloxyhydroxypropyltriethylammonium chloride.

The basic monomers can also be cationized, by neutralizing them with mineral acids, such as, for example, sulfuric acid, hydrochloric acid, hydrobromic acid, hydroiodic acid, phosphoric acid or nitric acid, or with organic acids, such as, for example, formic acid, acetic acid, lactic acid, or citric acid.

In addition to the abovementioned comonomers, it is also possible to use, as comonomers (c), so-called macromonomers such as, for example, silicone-containing macromonomers having one or more free-radically polymerizable groups or alkyloxazoline macromonomers, as described, for example, in EP 408 311.

Furthermore, it is possible to use fluorine-containing monomers, as described, for example, in EP 558423, crosslinking compounds or compounds which regulate the molecular weight, in combination or alone.

Regulators which can be used are the customary compounds known to the person skilled in the art, such as, for example, sulfur compounds (e.g. mercaptoethanol, 2-ethylhexyl thioglycolate, thioglycolic acid or dodecylmercaptan), and tribromochloromethane and other compounds which have a regulating effect on the molecular weight of the resulting polymers.

In some instances, it is also possible to use thio-containing silicone compounds.

Preference is given to using silicone-free regulators.

Crosslinking monomers which can be used are compounds having at least two ethylenically unsaturated double bonds, such as, for example, esters of ethylenically unsaturated carboxylic acids, such as acrylic acid or methacrylic acid and polyhydric alcohols, ethers of at least dihydric alcohols such as, for example, vinyl ethers or allyl ethers.

Examples of the parent alcohols are dihydric alcohols such as 1,2-ethanediol, 1,2-propanediol, 1,3-propanediol, 1,2-butanediol, 1,3-butanediol, 2,3-butanediol, 1,4-butanediol, but-2-ene-1,4-diol, 1,2-pentanediol, 1,5-pentanediol, 1,2-hexanediol, 1,6-hexanediol, 1,10-decanediol, 1,2-dodecanediol, 1,12-dodecanediol, neopentyl glycol, 3-methylpentane-1,5-diol, 2,5-dimethyl-1,3-hexanediol, 2,2,4-trimethyl-1,3-pentanediol, 1,2-cyclohexanediol, 1,4-cyclohexanediol, 1,4-bis(hydroxymethyl)cyclohexane, neopentyl glycol hydroxypivalate, 2,2-bis(4-hydroxyphenyl)propane, 2,2-bis[4-(2-hydroxypropyl)phenyl]propane, diethylene glycol, triethylene glycol, tetraethylene glycol, dipropylene glycol, tripropylene glycol, tetrapropylene glycol, 3-thiopentane-1,5-diol, and polyethylene glycols, polypropylene glycols and polytetrahydrofurans having molecular weights of in each case 200 to 10 000. Apart from the homopolymers of ethylene oxide and propylene oxide, it is also possible to use block copolymers of ethylene oxide or propylene oxide or copolymers which contain ethylene oxide and propylene oxide groups in incorporated form. Examples of parent alcohols having more than two OH groups are trimethylolpropane, glycerol, pentaerythritol, 1,2,5-pentanetriol, 1,2,6-hexanetriol, triethoxycyanuric acid, sorbitan, sugars such as sucrose, glucose, mannose. It is of course also possible to use the polyhydric alcohols following reaction with ethylene oxide or propylene oxide, as the corresponding ethoxylates or propoxylates respectively. The polyhydric alcohols can also firstly be converted into the corresponding glycidyl ethers by reaction with epichlorohydrin.

Further suitable crosslinkers are the vinyl esters or the esters of monohydric, unsaturated alcohols with ethylenically unsaturated $C_3$- to $C_6$-carboxylic acids, for example acrylic acid, methacrylic acid, itaconic acid, maleic acid or fumaric acid. Examples of such alcohols are allyl alcohol, 1-buten-3-ol, 5-hexen-1-ol, 1-octen-3-ol, 9-decen-1-ol, dicyclopentenyl alcohol, 10-undecen-1-ol, cinnamyl alcohol, citronellol, crotyl alcohol or cis-9-octadecen-1-ol. However, it is also possible to esterify the monohydric, unsaturated alcohols with polybasic carboxylic acids, for example malonic acid, tartaric acid, trimellitic acid, phthalic acid, terephthalic acid, citric acid or succinic acid.

Further suitable crosslinkers are esters of unsaturated carboxylic acids with the above-described polyhydric alcohols, for example of oleic acid, crotonic acid, cinnamic acid or 10-undecenoic acid.

Also suitable are straight-chain or branched, linear or cyclic aliphatic or aromatic hydrocarbons which have at least two double bonds which, in the case of aliphatic hydrocarbons, must not be conjugated, e.g., divinylbenzene, divinyltoluene, 1,7-octadiene, 1,9-decadiene, 4-vinyl-1-cyclohexene, trivinylcyclohexane or polybutadienes having molecular weights of from 200 to 20 000.

Also suitable are amides of unsaturated carboxylic acids, such as, for example, acrylic acid and methacrylic acid, itaconic acid, maleic acid and N-allylamines of at least difunctional amines, such as, for example, 1,2-diaminomethane, 1,2-diaminoethane, 1,3-diaminopropane, 1,4-diaminobutane, 1,6-diaminohexane, 1,12-dodecanediamine, piperazine, diethylenetriamine or isophorone diamine. Also suitable are the amides of allylamine and unsaturated carboxylic acids such as acrylic acid, methacrylic acid, itaconic acid, maleic acid, or at least dibasic carboxylic acids as have been described above.

Further suitable crosslinkers are triallylamine or corresponding ammonium salts, e.g. triallylmethylammonium chloride or triallylmethylammonium methyl sulfate.

It is also possible to use the N-vinyl compounds of urea derivatives, at least difunctional amides, cyanurates or urethanes, for example of urea, ethyleneurea, propyleneurea or tartramide, e.g. N,N'-divinylethyleneurea or N,N'-divinylpropyleneurea.

Further suitable crosslinkers are divinyldioxane, tetraallylsilane or tetravinylsilane.

Particularly preferred crosslinkers are, for example, methylenebisacrylamide, divinylbenzene, triallylamine and triallylammonium salts, divinylimidazole, N,N'-divinylethyleneurea, reaction products of polyhydric alcohols with acrylic acid or methacrylic acid, methacrylic esters and acrylic esters of polyalkylene oxides or polyhydric alcohols which have been reacted with ethylene oxide and/or propylene oxide and/or epichlorohydrin, and allyl or vinyl ethers of polyhydric alcohols, for example 1,2-ethanediol, 1,4-butanediol, diethylene glycol, trimethylolpropane, glycerol, pentaerythritol, sorbitan and sugars such as sucrose, glucose, mannose.

Very particularly preferred crosslinkers are pentaerythritol triallyl ethers, allyl ethers of sugars such as sucrose, glucose, mannose, divinylbenzene, methylenebisacrylamide, N,N'-divinylethyleneurea, and (meth)acrylic esters of glycol, butanediol, trimethylolpropane or glycerol or (meth) acrylic esters of glycol, butanediol, trimethylolpropane or glycerol reacted with ethylene oxide and/or epichlorohydrin.

The proportion of monomers which have a crosslinking action is 0 to 10% by weight, preferably 0.1 to 5% by weight, very particularly preferably 0.2 to 2% by weight.

In the polymerization for the preparation of the polymers according to the invention, in some instances it is also possible for other polymers, such as, for example, polyamides, polyurethanes, polyesters, homo- and copolymers of ethylenically unsaturated monomers, to be present. Examples of such polymers, some of which are also used in cosmetics, are the polymers known under the tradenames Amerhold™, Ultrahold™, Ultrahold Strong™, Luviflex™ VBM, Luvimer™, Acronal™, Acudyne™, Stepanhold™, Lovocryl™, Versatyl™, Amphomer™ or Eastma AQ™.

The comonomers (c) according to the invention can, provided they contain ionizable groups, be partially or completely neutralized using acids or bases before or after the polymerization in order, for example, to adjust the solubility or dispersibility in water to a desired degree.

Neutralizing agents for monomers carrying acid groups which can be used are, for example, mineral bases such as sodium carbonate, alkali metal hydroxides and ammonia, organic bases such as aminoalcohols, specifically 2-amino-2-methyl-1-propanol, monoethanolamine, diethanolamine, triethanolamine, triisopropanolamine, tri[(2-hydroxy)1-propyl]amine, 2-amino-2-methyl-1,3-propanediol, 2-amino-2-hydroxymethyl1,3-propanediol and diamines, such as, for example, lysine.

To prepare the polymers, the monomers of component a) can be polymerized in the presence of the polyethers either using initiators which form free radicals, or by the action of high-energy radiation, which is also intended to mean the action of high-energy electrons.

Initiators which can be used for the free-radical polymerization are the peroxo and/or azo compounds customary for this purpose, for example alkali metal or ammonium peroxydisulfates, diacetyl peroxide, dibenzoyl peroxide, succinyl peroxide, di-tert-butyl peroxide, tert-butyl perbenzoate, tert-butyl perpivalate, tert-butyl peroxy-2-ethylhexanoate, tert-butyl permaleate, cumene hydroperoxide, diisopropyl peroxydicarbamate, bis-(o-toluoyl) peroxide, didecanoyl peroxide, dioctanoyl peroxide, dilauroyl peroxide, tert-butyl perisobutyrate, tert-butyl peracetate, di-tert-amyl peroxide, tert-butyl hydroperoxide, azobisisobutyronitrile, azobis-(2-amidinopropane) dihydrochloride or 2,2'-azobis(2-methyl-butyronitrile). Also suitable are initiator mixtures or redox initiator systems, such as, for example, ascorbic acid/iron(II) sulfate/sodium peroxodisulfate, tert-butyl hydroperoxide/sodium disulfite, tert-butyl hydroperoxide/sodium hydroxymethanesulfinate. Preference is given to using organic peroxides.

The amounts of initiator or initiator mixtures used, based on monomer used, are between 0.01 and 10% by weight, preferably between 0.1 and 5% by weight.

The polymerization is carried out in a temperature range from 40 to 200° C., preferably in the range from 50 to 140° C., particularly preferably in the range from 60 to 110° C. It is usually carried out under atmospheric pressure, but can also be carried out under reduced or increased pressure, preferably between 1 and 5 bar.

The polymerization can, for example, be carried out as solution polymerization, bulk polymerization, emulsion polymerization, inverse emulsion polymerization, suspension polymerization, inverse suspension polymerization or precipitation polymerization, without the possible methods being limited thereto.

In the case of bulk polymerization, the procedure may involve dissolving the polyether-containing compound b) in at least one monomer of group a) and possibly other comonomers of group c) and, after the addition of a polymerization initiator, fully polymerizing the mixture. The polymerization can also be carried out semicontinuously by firstly introducing some, e.g. 10%, of the mixture to be polymerized comprising the polyether-containing compound b), at least one monomer from group a), possibly other comonomers of group c) and initiator, heating the mixture to the polymerization temperature and after the polymerization has started, adding the remainder of the mixture to be polymerized in accordance with the progress of the polymerization. The polymers can also be obtained by initially introducing the polyether-containing compounds of group b) into a reactor, heating them to the polymerization temperature and adding at least one monomer of group a), possibly other comonomers of group c) and polymerization initiator either in one portion, step by step or, preferably, continuously, and polymerizing.

If desired, the above described polymerization can also be carried out in a solvent. Suitable solvents are, for example, alcohols, such as methanol, ethanol, n-propanol, isopropanol, n-butanol, sec-butanol, tert-butanol, n-hexanol and cyclohexanol, and glycols, such as ethylene glycol, propylene glycol and butylene glycol, and the methyl or ethyl ethers of dihydric alcohols, diethylene glycol, triethylene glycol, glycerol and dioxane. The polymerization can also be carried out in water as solvent. In this case, the initial batch is a solution which, depending on the amount of monomers of component a) added, is soluble in water to a greater or lesser degree. In order to convert water-insoluble products, which can form during the polymerization, into solution, it is possible, for example, to add organic solvents, such as monohydric alcohols having from 1 to 3 carbon atoms, acetone or dimethylformamide. However, in the case of polymerization in water, it is also possible to convert the water-insoluble polymers into a finely divided dispersion by addition of customary emulsifiers or protective colloids, e.g. polyvinyl alcohol.

The emulsifiers used are, for example, ionic or nonionic surfactants whose HLB value is in the range from 3 to 13.

The definition of the HLB value can be found in the publication by W. C. Griffin, J. Soc. Cosmetic Chem., Volume 5, 249 (1954).

The amount of surfactants, based on the polymer, is from 0.1 to 10% by weight. Using water as solvent gives solutions or dispersions of the polymers. If solutions of the polymer are prepared in an organic solvent or in mixtures of an organic solvent and water, then, per 100 parts by weight of the polymer, from 5 to 2000, preferably from 10 to 500, parts by weight of the organic solvent or of the solvent mixture are used.

Preference is given to polymers obtainable by free-radical polymerization of a) 10–98% by weight of at least one vinyl ester of $C_1$–$C_{24}$ carboxylic acids in the presence of b) 2–90% by weight of at least one polyether-containing compound and c) 0–50% by weight of one or more other copolymerizable monomers.

Particular preference is given to polymers obtainable by free-radical polymerization of a) 50–97% by weight of at least one vinyl ester of $C_1$–$C_{24}$ carboxylic acids in the presence of b) 3–50% by weight of at least one polyether-containing compound and c) 0–30% by weight of one or more other copolymerizable monomers.

Very particular preference is given to polymers obtainable by free-radical polymerization of a) 60–97% by weight of at least one vinyl ester of $C_1$–$C_{24}$ carboxylic acids in the presence of b) 3–40% by weight of at least one polyether-containing compound and c) 0–20% by weight of one or more other copolymerizable monomers.

To prepare the polymers used according to the invention, the ester groups of the original monomers a) and optionally of other monomers are cleaved after the polymerization by hydrolysis, alcoholysis, or aminolysis. This process step is generally referred to below as hydrolysis. The hydrolysis takes place in a manner known per se by the addition of a base, preferably the addition of a sodium or potassium hydroxide solution in water and/or alcohol. Particular preference is given to using methanolic sodium or potassium hydroxide solutions. The hydrolysis is carried out at temperatures in the range from 10 to 80° C., preferably in the range from 20 to 60° C. The degree of hydrolysis depends on the amount of base used, on the hydrolysis temperature, on the hydrolysis time and the water content of the solution.

The degree of hydrolysis of the polyvinyl ester groups is in the range from 1 to 100%, preferably in the range from 40 to 100%, particularly preferably in the range from 65 to 100%, very particularly preferably in the range from 80 to 100%.

The polymers prepared in this way can then be cationized by reaction of hydroxyl and/or amino functions present in the polymer with epoxides of the formula VI ($R^{26}$=$C_1$- to $C_{40}$-alkyl).

(VI)

For this, the hydroxyl groups of the polyvinyl alcohol units and vinylamine units, formed by hydrolysis of vinylformamide, can preferably be reacted with the epoxides.

The epoxides of the formula VI can also be produced in situ by reaction of the corresponding chlorohydrins with bases, for example sodium hydroxide.

Preference is given to using 2,3-epoxypropyltrimethylammonium chloride or 3-chloro-2-hydroxypropyltrimethylammonium chloride. The K values of the polymers should be in the range from 10 to 300, preferably 25 to 250, particularly preferably 25 to 200, very particularly preferably in the range from 30 to 150. The K value desired in each case can be adjusted in a manner known per se through the composition of the feed substances. The K values are determined in accordance with Fikentscher, Cellulosechemie, Vol. 13, p. 58 to 64, and 71 to 74 (1932) in N-methylpyrrolidone at 25° C. and polymer concentrations which, depending on the K value range, are between 0.1% by weight and 5% by weight.

After the hydrolysis, the polymer solutions can be steam distilled to remove any solvents. After the steam distillation, aqueous solutions or dispersions are obtained depending on the degree of hydrolysis, type of polyethers b), of vinyl esters a) and any monomers c) used.

The polymers obtained can also be subsequently crosslinked by reacting the hydroxyl groups or amino groups in the polymer with at least bifunctional reagents. In the case of low degrees of crosslinking, water-soluble products are obtained, and in the case of high degrees of crosslinking, water-swellable or insoluble products are obtained.

For example, the polymers according to the invention can be reacted with aldehydes, dialdehydes, ketones and diketones, e.g. formaldehydes, acetaldehyde, glyoxal, glutaraldehyde, succindialdehyde or terephthalaldehyde. Also suitable are aliphatic or aromatic carboxylic acids, for example maleic acid, oxalic acid, malonic acid, succinic acid or citric acid, or carboxylic acid derivatives, such as carboxylic esters, anhydrides or halides. Also suitable are polyfunctional epoxides, e.g. epichlorohydrin, glycidyl methacrylate, ethylene glycol diglycidyl ether, 1,4-butanediol diglycidyl ether or 1,4-bis(glycidyloxy)benzene. Also suitable are diisocyanates, for example hexamethylene diisocyanate, isophorone diisocyanate, methylenediphenyl diisocyanate, toluylene diisocyanate or divinylsulfone.

Also suitable are inorganic compounds, such as boric acid or boric acid salts, which are referred to collectively as borates below, for example sodium metaborate, borax (disodium tetraborate), and salts of polyvalent cations, e.g. copper(II) salts, such as copper(II) acetate or zinc, aluminum, titanium salts.

Boric acid and/or boric acid salts, such as sodium metaborate or disodium tetraborate, are preferably suitable for the subsequent crosslinking. In this connection, boric acid and/or boric acid salts can, preferably as salt solutions, be added to the solutions of the polymers according to the invention. Preference is given to adding boric acid and/or boric acid salts to the aqueous polymer solutions.

The boric acid and/or boric acid salts can be added to the polymer solutions directly after preparation. It is, however, also possible to add the boric acid and/or boric acid salts subsequently to the cosmetic formulations containing the polymers according to the invention, or to add them during the preparation process of the cosmetic formulations.

The proportion of boric acid and/or boric acid salts, based on the polymers according to the invention, is 0 to 15% by weight, preferably 0 to 10% by weight, particularly preferably 0 to 5% by weight.

The polymer solutions and dispersions can be converted into powder form by a variety of drying methods, such as, for example, spray drying, fluidized spray drying, drum drying or freeze drying. The drying method used in preference is spray drying. The dry polymer powder obtained in this way can be used to prepare an aqueous solution or dispersion again, by dissolution or redispersion in water. Conversion into powder form has the advantage of better storability, easier transportation, and a lower propensity for microbial attack.

Instead of the steam distilled polymer solutions, the alcoholic polymer solutions can also be directly converted into powder form.

The water-soluble or water-dispersible polyalkylene oxide- or polyglycerol-containing polymers according to the invention are highly suitable for use in hair cosmetic formulations.

The polymers according to the invention, prepared by free-radical polymerization of vinyl esters and optionally other polymerizable monomers in the presence of polyether-containing compounds and subsequent at least partial hydrolysis of the ester functions of the original vinyl esters, are suitable as styling agents and/or conditioning agents in hair cosmetic preparations such as hair treatments, hair lotions, hair rinses, hair emulsions, fluids for treating hair ends, neutralizing agents for permanent waves, "hot-oil-treatment" preparations, conditioners, setting lotions or hairsprays. Depending on the area of application, the hair cosmetic preparations can be applied as a spray, foam, gel, gel spray or mousse.

The hair cosmetic formulations according to the invention comprise, in a preferred embodiment,
a) 0.05–20% by weight of the polymer according to the invention, prepared by free-radical polymerization of vinyl esters and optionally other polymerizable monomers in the presence of polyether-containing compounds and subsequent at least partial hydrolysis of the ester functions of the original vinyl esters
b) 20–99.95% by weight of water and/or alcohol
c) 0–79.5% by weight of other constituents Alcohol is taken to mean all alcohols customary in cosmetics, e.g. ethanol, isopropanol, n-propanol.

Other constituents are taken to mean the additives customary in cosmetics, for example propellants, antifoams, surface-active compounds, i.e. surfactants, emulsifiers, foam formers and solubilizers. The surface-active compounds used can be anionic, cationic, amphoteric or neutral. In addition, other customary constituents can be, for example, preservatives, perfume oils, opacifiers, active ingredients, UV filters, care substances such as panthenol, collagen, vitamins, protein hydrolysates, alpha- and beta-hydroxycarboxylic acids, stabilizers, pH regulators, dyes, viscosity regulators, gel formers, salts, humectants, refatting agents and other customary additives.

These also include all styling and conditioning polymers known in cosmetics which can be used in combination with the polymers according to the invention, in cases where very specific properties are to be set.

Suitable traditional hair cosmetic polymers are, for example, anionic polymers. Such anionic polymers are homo- and copolymers of acrylic acid and methacrylic acid or salts thereof, copolymers of acrylic acid and acrylamide and salts thereof; sodium salts of polyhydroxycarboxylic acids, water-soluble or water-dispersible polyesters, polyurethanes (Luviset® P.U.R.) and polyureas. Particularly suitable polymers are copolymers of t-butyl acrylate, ethyl acrylate, methacrylic acid (e.g. Luvimer® 100P), copolymers of N-tert-butylacrylamide, ethyl acrylate, acrylic acid (Ultrahold® 8, strong), copolymers of vinyl acetate, crotonic acid and optionally other vinyl esters (e.g. Luviset® grades), maleic anhydride copolymers, optionally reacted with alcohols, anionic polysiloxanes, e.g. carboxy-functional ones, copolymers of vinylpyrrolidone, t-butyl acrylate, methacrylic acid (e.g. Luviskol® VBM).

Very particularly preferred anionic polymers are acrylates with an acid number greater than or equal to 120 and copolymers of t-butyl acrylate, ethyl acrylate and methacrylic acid.

Other suitable hair cosmetic polymers are cationic polymers with the name polyquaternium according to INCI, e.g. copolymers of vinylpyrrolidone/N-vinylimidazolium salts (Luviquat® FC, Luviquat® HM, Luviquat® MS, Luviquat® Care), copolymers of N-vinylpyrrolidone/dimethylaminoethyl methacrylate, quaternized with diethylsulfate (Luviquat® PQ 11), copolymers of N-vinylcaprolactam-N-vinylpyrrolidone/N-vinylimidazolium salts (Luviquat® Hold); cationic cellulose derivatives (polyquaternium-4 and -10), acrylamide copolymers (polyquaternium-7).

Other suitable hair cosmetic polymers are also neutral polymers such as polyvinylpyrrolidones, copolymers of N-vinylpyrrolidone and vinyl acetate and/or vinyl propionate, polysiloxanes, polyvinylcaprolactam and copolymers with N-vinylpyrrolidone, polyethyleneimines and salts thereof, polyvinylamines and salts thereof, cellulose derivatives, polyaspartic acid salts and derivatives.

To establish certain properties, the preparations can also additionally comprise conditioning substances based on silicone compounds. Suitable silicone compounds are, for example, polyalkylsiloxanes, polyarylsiloxanes, polyarylalkylsiloxanes, polyethersiloxanes, silicone resins or dimethicone copolyols (CTFA) and amino-functional silicone compounds such as Amodimethicones (CTFA).

The polymers according to the invention are particularly suitable as setting agents in hair styling preparations, in particular hairsprays (aerosols and pump sprays without propellant) and hair foams (aerosol foams and pump foams without propellant). In a preferred embodiment, these preparations comprise
a) 0.1–10% by weight of the polymer according to the invention, prepared by free-radical polymerization of vinyl esters and optionally other polymerizable monomers in the presence of polyether-containing compounds and subsequent at least partial hydrolysis of the ester functions of the original vinyl esters
b) 20–99.9% by weight of water and/or alcohol
c) 0–70% by weight of a propellant
d) 0–20% by weight of other constituents.

The propellants are those customarily used for hairsprays or aerosol foams. Preference is given to mixtures of propane/butane, pentane, dimethyl ether, 1,1-difluoroethane (HFC-152 a), carbon dioxide, nitrogen or compressed air.

A formulation preferred according to the invention for aerosol hair foams comprises
a) 0.1–10% by weight of the polymer according to the invention, prepared by free-radical polymerization of vinyl esters and optionally other polymerizable monomers in the presence of polyether-containing compounds and subsequent at least partial hydrolysis of the ester functions of the original vinyl esters
b) 55–94.8% by weight of water and/or alcohol
c) 5–20% by weight of a propellant
d) 0.1–5% by weight of an emulsifier
e) 0–10% by weight of other constituents.

The emulsifiers can be any emulsifiers customarily used in hair foams. Suitable emulsifiers can be nonionic, cationic or anionic.

Examples of nonionic emulsifiers (INCI nomenclature) are laureths, e.g. laureth-4; ceteths, e.g. cetheth-1, polyethylene glycol cetyl ether; cetearths, e.g. cetheareth-25, polyglycol fatty acid glycerides, hydroxylated lecithin, lactyl esters of fatty acids, alkylpolyglycosides.

Examples of cationic emulsifiers are cetyldimethyl-2-hydroxyethylammonium dihydrogenphosphate, cetyltrimonium chloride, cetyltrimonium bromide, cocotrimonium methylsulfate, quaternium-1 to x (INCI).

Anionic emulsifiers can, for example, be chosen from the group consisting of alkylsulfates, alkyl ether sulfates, alkylsulfonates, alkylarylsulfonates, alkylsuccinates, alkylsulfosuccinates, N-alkoylsarcosinates, acyltaurates, acylisethionates, alkylphosphates, alkyl ether phosphates, alkyl ether carboxylates, alpha-olefin sulfonates, in particular the alkali metal and alkaline earth metal salts, e.g. sodium, potassium, magnesium, calcium, and ammonium and triethanolamine salts. The alkyl ether sulfates, alkyl ether phosphates and alkyl ether carboxylates can have between 1 and 10 ethylene oxide or propylene oxide units, preferably from 1 to 3 ethylene oxide units, in the molecule.

A preparation which is suitable according to the invention for styling gels can, for example, have the following composition:

a) 0.1–10% by weight of the polymer according to the invention, prepared by free-radical polymerization of vinyl esters and optionally other polymerizable monomers in the presence of polyether-containing compounds and subsequent at least partial hydrolysis of the ester functions of the original vinyl esters
b) 60–99.85% by weight of water and/or alcohol
c) 0.05–10% by weight of a gel former
d) 0–20% by weight of other constituents.

The gel formers which can be used are any gel formers customary in cosmetics. These include totally crosslinked polyacrylic acid, for example carbomer (INCI), cellulose derivatives, e.g. hydroxypropylcellulose, hydroxyethylcellulose, cationically modified celluloses, polysaccharides, e.g. xanthan gum, caprylic/capric triglycerides, sodium acrylates copolymer, polyquaternium-32 (and) paraffinum liquidum (INCI), sodium acrylates copolymer (and) paraffinum liquidum (and) PPG-1 trideceth-6, acrylamidopropyltrimonium chloride/acrylamide copolymer, steareth-10 allyl ether acrylates copolymer, polyquaternium-37 (and) paraffinum liquidum (and) PPG-1 trideceth-6, polyquaternium 37 (and) propylene glycole dicaprate dicaprylate (and) PPG-1 trideceth-6, polyquaternium-7, polyquaternium-44.

The polymers according to the invention can also be used in shampoo formulations as setting and/or conditioning agents. Suitable conditioning agents are, in particular, polymers with a cationic charge.

Preferred shampoo formulations comprise a) 0.05–10% by weight of the polymer according to the invention, prepared by free-radical polymerization of vinyl esters and optionally other polymerizable monomers in the presence of polyether-containing compounds and subsequent at least partial hydrolysis of the ester functions of the original vinyl esters
b) 25–94.95% by weight of water
c) 5–50% by weight of surfactants
c) 0–5% by weight of another conditioning agent
d) 0–10% by weight of other cosmetic constituents.

In the shampoo formulations, it is possible to use all anionic, neutral, amphoteric or cationic surfactants used customarily in shampoos.

Suitable anionic surfactants are, for example, alkylsulfates, alkyl ether sulfates, alkylsulfonates, alkylarylsulfonates, alkylsuccinates, alkylsulfosuccinates, N-alkoylsarcosinates, acyltaurates, acylisethionates, alkylphosphates, alkyl ether phosphates, alkyl ether carboxylates, alpha-olefinsulfonates, in particular the alkali metal and alkaline earth metal salts, e.g. sodium, potassium, magnesium, calcium, and ammonium and triethanolamine salts. The alkyl ether sulfates, alkyl ether phosphates and alkyl ether carboxylates can have between 1 and 10 ethylene oxide or propylene oxide units, preferably from 1 to 3 ethylene oxide units, in the molecule.

Suitable examples are sodium laurylsulfate, ammonium laurylsulfate, sodium lauryl ether sulfate, ammonium lauryl ether sulfate, sodium lauroyl sarcosinate, sodium oleyl succinate, ammonium lauryl sulfosuccinate, sodium dodecylbenzenesulfonate, triethanolamine dodecylbenzenesulfonate.

Suitable amphoteric surfactants are, for example, alkylbetaines, alkylamidopropylbetaines, alkylsulfobetaines, alkylglycinates, alkylcarboxyglycinates, alkylamphoacetates or -propionates, alkylamphodiacetates or -dipropionates.

It is, for example, possible to use cocodimethylsulfopropylbetaine, laurylbetaine, cocamidopropylbetaine or sodium cocamphopropionate.

Examples of suitable nonionic surfactants are the reaction products of aliphatic alcohols or alkyl phenols having from 6 to 20 carbon atoms in the alkyl chain, which can be linear or branched, with ethylene oxide and/or propylene oxide. The amount of alkylene oxide is from about 6 to 60 mole per mole of alcohol. Also suitable are alkylamine oxides, mono- or dialkyl alkanolamides, fatty acid esters of polyethylene glycols, alkyl polyglycosides or sorbitan ether esters.

The shampoo formulations can also comprise customary cationic surfactants, such as, for example, quaternary ammonium compounds, for example cetyltrimethylammonium chloride.

To achieve certain effects, customary conditioning agents can be used in combination with the polymers according to the invention in the shampoo formulations. Such conditioning agents include, for example, cationic polymers with the name polyquaternium according to INCI, in particular copolymers of vinylpyrrolidone/N-vinylimidazolium salts (Luviquat® FC, Luviquat® HM, Luviquat® MS, Luviquat® Care), copolymers of N-vinylpyrrolidone/dimethylaminoethyl methacrylate, quaternized with diethyl sulfate (Luviquat® PQ 11), copolymers of N-vinylcaprolactam/N-vinylpyrrolidone/N-vinylimidazolium salts (Luviquat® Hold); cationic cellulose derivatives (polyquaternium-4 and -10), acrylamide copolymers (polyquaternium-7). In addition, it is also possible to use protein hydrolysates, and conditioning substances based on silicone compounds, for example polyalkylsiloxanes, polyarylsiloxanes, polyarylalkylsiloxanes, polyether siloxanes or silicone resins. Other suitable silicone compounds are Dimethicone Copolyols (CTFA) and amino-functional silicone compounds such as Amodimethicones (CTFA).

The invention further provides polymers obtainable by free-radical polymerization of a) at least one vinyl ester of a $C_1$–$C_{24}$-carboxylic acid, in the presence of b) polyether-containing silicone derivatives and c) optionally one or more other copolymerizable monomers and subsequent at least partial hydrolysis of the ester functions of the original vinyl esters.

Preference is given to polymers obtainable by free-radical polymerization of a) at least one vinyl ester of a $C_1$–$C_{24}$-carboxylic acid, in the presence of b) polyether-containing silicone derivatives which contain the following structural elements:

$$R^{10}\!-\!\!\begin{bmatrix}R^8\\|\\Si\!-\!O\\|\\R^8\end{bmatrix}_a\!\!\begin{bmatrix}R^8\\|\\Si\!-\!O\\|\\R^8\end{bmatrix}_b\!\!\begin{matrix}R^8\\|\\Si\!-\!R^9\\|\\R^8\end{matrix} \qquad \text{II}$$

where:

$R^9 = CH_3$ or $\ \diagdown\!O\!\diagup\!\!\diagdown\!\!\diagup\!\Big[\!O\!\Big]_c\!\Big[\!\diagdown\!\!\diagup\!O\!\Big]_d\!R^{11}$ $R^{10} = CH_3$ or $R^9$ $R^{11} = H, CH_3,\ \ -\!\!\begin{bmatrix}R^8\\|\\Si\!-\!O\\|\\R^8\end{bmatrix}_a\!\!\begin{matrix}R^8\\|\\Si\!-\!CH_3\\|\\R^8\end{matrix}$ $-\!\!\Big(\!\overset{\overset{O}{\|}}{C}\!\Big)_{\!e}\!-\!R^{13}$ $R^{13}$ is a $C_{1\text{-}40}$ organic radical which can contain amino, carboxyl or sulfonate groups, or where e=0, is also the anion of an inorganic acid, and where the radicals $R^8$ can be identical or different, and come either from the group of aliphatic hydrocarbons having from 1 to 20 carbon atoms, are cyclic aliphatic hydrocarbons having from 3 to 20 carbon atoms, are of an aromatic nature or are identical to $R^{12}$, where:

$R^{12} = \ -\!(CH_2)_f\!-\!O\!\diagup\!\!\diagdown\!\!\diagup\!\Big[\!O\!\Big]_c\!\Big[\!\diagdown\!\!\diagup\!O\!\Big]_d\!R^{11}$ with the proviso that at least one of the radicals $R^8$, $R^9$ or $R^{10}$ is a polyalkylene oxide-containing radical as defined above, and f is an integer from 1 to 6, a and b are integers such that the molecular weight of the polysiloxane block is between 300 and 30000, c and d can be integers between 0 and 50, with the proviso that the sum c+d is greater than 0, and e is 0 or 1, and c) optionally one or more other copolymerizable monomers and subsequent at least partial hydrolysis of the vinyl ester functions of the original vinyl esters. Very particular preference is given to polymers obtainable by free-radical polymerization of a) at least one vinyl ester of a $C_1$–$C_{24}$-carboxylic acid, in the presence of b) polyether-containing silicone derivatives of the structure:

$$CH_3\!-\!\!\begin{bmatrix}R^8\\|\\Si\!-\!O\\|\\R^8\end{bmatrix}_a\!\!\begin{bmatrix}R^8\\|\\Si\!-\!O\\|\\R^{12}\end{bmatrix}_b\!\!\begin{matrix}CH_3\\|\\Si\!-\!CH_3\\|\\CH_3\end{matrix}$$

and c) optionally one or more other copolymerizable monomers and subsequent at least partial hydrolysis of the ester functions of the original vinyl esters a).

The invention further provides polymers obtainable by free-radical polymerization of a) a vinyl ester of a $C_1$–$C_{24}$ carboxylic acid in the presence of b) polyether-containing compounds obtainable by reaction of polyethyleneimines with alkylene oxides and c) optionally one or more other copolymerizable monomers and subsequent at least partial hydrolysis of the ester functions of the original vinyl esters.

The invention further provides polymers obtainable by free-radical polymerization of a) a vinyl ester of a $C_1$–$C_{24}$ carboxylic acid in the presence of b) homo- and copolymers of ethylenically unsaturated polyether-containing compounds and c) optionally one or more other copolymerizable monomers and subsequent at least partial hydrolysis of the ester functions of the original vinyl esters.

The invention further provides crosslinked polymeres obtainable by free-radical polymerization of a) at least one vinyl ester of $C_1$–$C_{24}$ carboxylic acids in the presence of b) polyether-containing compounds and c) optionally one or more further copolymerizable monomers and subsequent at least partial hydrolysis of the ester functions of the original monomers a), where the crosslinker used is either already present during the polymerization, or is added after the polymerization and hydrolysis.

PREPARATION EXAMPLES

Preparation Procedure for Examples 1 to 26

The polyether-containing compound is heated to 80° C. in a polymerization vessel with stirring and under a gentle stream of nitrogen. With stirring, vinyl acetate and optionally the other monomers are metered in over the course of 3 h. At the same time, a solution of 1.4 g of tert-butyl perpivalate in 30 g of methanol is likewise added over 3 h. The mixture is then stirred for a further 2 h at 80° C. After cooling, the polymer is dissolved in 450 ml of methanol. For hydrolysis, 50 ml of a 10% strength methanolic sodium hydroxide solution are added at 30° C. After about 40 min., the reaction is terminated by addition of 750 ml of 1% strength acetic acid. The methanol is removed by distillation.

The K values were determined at a concentration of 1% in N-methylpyrrolidone.

TABLE

| Example | Graft base | Vinyl ester | Comonomer | K value | Degree of hydrolysis [%] |
|---|---|---|---|---|---|
| 1 | PEG 1500[1], 72 g | vinyl acetate, 410 g | — | 47 | >95 |
| 2 | PEG 4000, 72 g | vinyl acetate, 410 g | — | 51 | >95 |
| 3 | PEG 6000, 72 g | vinyl acetate, 410 g | — | 54 | >95 |
| 4 | PEG 6000, 137 g | vinyl acetate, 410 g | | 49 | >95 |
| 5 | PEG 6000, 22 g | vinyl acetate, 410 g | — | 73 | >95 |
| 6 | PEG 6000, 410 g | vinyl acetate, 410 g | | 42 | >95 |
| 7 | PEG 9000, 137 g | vinyl acetate, 410 g | — | 58 | >95 |
| 8 | polyglycerol 2200, 72 g | vinyl acetate, 410 g | — | 66 | >95 |
| 9 | PEG-PPG block copolymer 8000[2], 72 g | vinyl acetate, 410 g | — | 45 | >95 |
| 10 | methylpolyethylene glycol 2000[3], 72 g | vinyl acetate, 410 g | — | 47 | >95 |
| 11 | alkylpolyethylene glycol 3500[4], 72 g | vinyl acetate, 410 g | — | 48 | >95 |
| 12 | PPG 4000[5], 72 g | vinyl acetate, 410 g | — | 50 | >95 |
| 13 | PEG 20000, 72 g | vinyl acetate, 410 g | — | 69 | >95 |
| 14 | PEG 20000, 103 g | vinyl acetate, 410 g | — | 64 | >95 |
| 15 | PEG 20000, 137 g | vinyl acetate, 410 g | — | 59 | >95 |
| 16 | PEG 20000, 615 g | vinyl acetate, 410 g | — | 55 | 86 |
| 17 | PEG 35000, 72 g | vinyl acetate, 410 g | — | 77 | >95 |
| 18 | PEG 35000, 137 g | vinyl acetate, 410 g | — | 80 | >95 |
| 19 | PEG 35000, 205 g | vinyl acetate, 410 g | — | 65 | 97 |
| 20 | dimethicone copolyol[16], 202 g | vinyl acetate, 410 g | — | 58 | >95 |
| 21 | poly(sodium methacrylate-co-methylpolyethylene glycol methacrylate)[7] 103 g | vinyl acetate, 410 g | | 43 | >95 |
| 22 | ethoxylated polyethyleneimine[8] | vinyl acetate, 410 g | | 52 | >95 |
| 23 | PEG 6000, 72 g | vinyl acetate, 386 g | methyl methacrylate, 24 g | 47 | >95 |
| 24 | PEG 20000, 72 g | vinyl acetate, 328 g | N-vinylpyrrolidone, 82 g | 61 | >95 |
| 25 | PEG 20000, 72 g | vinyl acetate, 362 g | 3-methyl-1-vinyl-imidazolium, methylsulfate, 48 g | 53 | >95 |
| 26 | PEG 6000, 72 g | vinyl acetate, 367 g | N-vinylformamide, 41 g | 57 | >95 |
| 27 | PEG 6000, 72 g | vinyl acetate, 326 g | N-vinylformamide, 82 g | 67 | >95 |
| 28 | PEG 35000, 270 g | vinyl acetate, 410 g | | 59 | 96 |
| 29 | PEG 35000, 270 g | vinyl acetate, 410 g | pentaerythritol triallyl ether, 1.6 g | 71 | 95 |
| 30 | PEG 35000 270 g | vinyl acetate, 410 g | pentaerythritol triallyl ether, 0.8 g | 65 | 94 |
| 31 | PEG 35000, 270 | vinyl acetate, 410 g | N,N'-divinyl-ethyleneurea, 0.7 g | 73 | 95 |

TABLE-continued

| Example | Graft base | Vinyl ester | Comonomer | K value | Degree of hydrolysis [%] |
|---|---|---|---|---|---|
| 32 | PEG 12000, 270 g | vinyl acetate, 410 g | pentaerythritol triallyl ether, 1.6 g | 50 | 94 |

[1]PEG x: polyethylene glycol with an average molecular weight x (weight average)
[2]Lutrol F 68 from BASF Aktiengesellschaft (PPG: polypropylene glycol)
[3]Pluriol A 2000 E from BASF Aktiengesellschaft
[4]Lutensol AT 80 from BASF Aktiengesellschaft ($C_{16}$–$C_{18}$ fatty alcohol + 80 EO)
[5]Polypropylene glycol with an average molecular weight of 4000
[6]Belsil DMC 6031TM from Wacker Chemie GmbH
[7]Molar ratio of sodium methacrylate/methylpolyethylene glycol methacrylate 4:1, methylpolyethylene glycol with a molar mass of about 1000
[8]Prepared from 12.5% of polyethyleneimine (average molecular weight 1400) and 87.5% of ethylene oxide

Example 33

Reaction with 3-chloro-2-hydroxypropyltrimethyl-ammonium Chloride 22 g of a 60% strength aqueous solution of 3-chloro-2-hydroxypropyltrimethylammonium chloride and 3.5 g of sodium hydroxide are added to 400 g of a 32.9% strength solution from Example 3. The mixture is stirred for 3 hours at 60° C. and then for a further two hours at 90° C., giving a clear solution.

Example 34

Reaction with 3-chloro-2-hydroxypropyltrimethyl-ammonium Chloride 46 g of a 60% strength aqueous solution of 3-chloro-2-hydroxypropyltrimethylammonium chloride and 6 g of sodium hydroxide are added to 400 g of a 15.3% strength solution from Example 26. The mixture is stirred for 3 hours at 60° C. and then for a further two hours at 90° C., giving a clear solution.

Example 35

At room temperature and with stirring, a 5% strength aqueous solution of disodium tetraborate decahydrate (borax) is added to a 19.3% strength aqueous solution of the polymer from example 28 over the course of half an hour. An increase in the viscosity is observed.

| Amount of 5% strength borax solution added [g] | Brookfield viscosity (LVF, spindle 2, 30 rpm, 23° C.) [mPas] |
|---|---|
| 0 | 110 |
| 14.9 | 128 |
| 18.0 | 216 |
| 21.0 | 534 |
| 24.0 | 2 228 |
| 26.9 | 7 520[1] |
| 29.8 | 29 190[2] |

[1]Spindle 4, 30 rpm
[2]Spindle 4, 6 rpm

1 Spindle 4, 30 rpm
2 Spindle 4, 6 rpm

FORMULATION EXAMPLES

Example 36

Aerosol Hair Foam Formulation 2.00% of copolymer from Example 3
2.00% of Luviquat Mono LS (cocotrimonium methylsulfate)
67.7% of water
10.0% of propane/butane 3.5 bar (20° C.)
q.s. perfume oil

Example 37

Comparative Example 2.00% polymer content Luviquat Hold (polyquaternium-46)
2.00% of Luviquat Mono LS (cocotrimonium methylsulfate)
67.7% of water
10.0% of propane/butane 3.5 bar (20° C.)
q.s. perfume oil Using Example 36 and Example 37 (Comparative Example), half-head tests were carried out on dummy heads. The assessment was subjectively carried out by trained hairdressers and laboratory assistants.

Scale of grades from 1 (very good) to 3 (poor)

|  | Example 36 | Example 37 (Comparative Example) |
|---|---|---|
| Foaming: | 1 | 1 |
| Consistency of the foam: | 1 | 1 |
| Dispersibility: | 1 | 1 |
| Wet hair feel: | 1− | 2 |
| Wet combability: | 1− | 2+ |
| Hold: | 1 | 2+ |
| Dry combability: | 2+ | 2 |
| Tack: | 1 | 1− |
| Dry hair feel: | 1− | 2+ |
| Hair elasticity: | 1 | 2− |

The formulation from Example 36 had better hold, better wet combability, lower tack and better hair elasticity than the formulation from Example 37 (Comparative Example).

Example 38

| | |
|---|---|
| 4.00% of copolymer from Example 19 | INCI |
| 0.20% of Cremophor A 25 | Ceteareth-25 |
| 1.00% of Luviquat Mono CP | Hydroxyethyl cetyldimonium phosphate |
| 5.00% of ethanol | |
| 1.00% of Panthenol | |
| 10.0% of propane/butane 3.5 bar (20° C.) | |
| q.s. perfume oil | |
| ad 100% with water | |

Example 39

Pump Foam

| | |
|---|---|
| 2.00% of copolymer from Example 7 | |
| 2.00% of Luviflex Soft (polymer content) | |
| 1.20% of 2-amino-2-methyl-1-propanol | |
| 0.20% of Cremophor A 25 | |
| 0.10% of Uvinul P 25 | PEG-25 PABA |
| q.s. preservative | |
| q.s. perfume oil | |
| ad 100% with water | |

Example 40

Pump Spray

| | |
|---|---|
| 4.00% of copolymer from Example 17 | |
| 1.00% of panthenol | |
| 0.10% of Uvinul MS 40 | Benzophenone-4 |
| q.s. preservative | |
| q.s. perfume oil | |
| ad 100% with water | |

Example 41

Pump Spray

| | |
|---|---|
| 4.00% of copolymer from Example 9 | |
| 1.00% of panthenol | |
| 0.10% of Uvinul M 40 | Benzophenone-3 |
| q.s. preservative | |
| q.s. perfume oil | |
| ad 100% with ethanol | |

Example 42

Hair Spray

| | |
|---|---|
| 5.00% of copolymer from Example 6 | |
| 0.10% of silicone oil Dow Corning DC 190 | Dimethicone Copolyol |
| 35.00% of dimethyl ether | |
| 5.00% of n-pentane | |
| ad 100% with ethanol | |
| q.s. perfume oil | |

Example 43

Hairspray VOC 55%

| | |
|---|---|
| 3.00% of copolymer from Example 4 | |
| 7.00% of Luviset P.U.R. | Polyurethane-1 |
| 40.00% of dimethyl ether | |
| 15.00% of ethanol | |
| q.s. perfume oil | |
| ad 100% with water | |

Example 44

Hair Gel

| | |
|---|---|
| 0.5% of Carbopol 980 | Carbomer |
| 3.00% of copolymer from example 18 | |
| 0.10% of phytantriol | |
| 0.50% of panthenol | |
| q.s. of perfume oil | |
| q.s. of preservative | |
| ad 100% with water | |

Example 45

Hair Shampoo or Shower Gel

| | |
|---|---|
| 0.5% of copolymer from example 33 | |
| 40.00% of Texapon NSO | Sodium Laureth Sulfate |
| 5.00% of Tego betaine L 7 | Cocamidopropyl Betaine |
| 5.00% of Plantacare 2000 | Decyl Glucoside |
| 1.00% of propylene glycol | |
| q.s. of citric acid | |
| q.s. of preservative | |
| 1.00% of sodium chloride | |
| ad 100% with water | |

We claim:

1. A method for improving hold or elasticity of a hairstyle, said method comprising applying to the hair polymers obtained by free-radical polymerization of
   a) at least one vinyl ester of $C_1$–$C_{24}$-carboxylic acids in the presence of
   b) polyether-containing compounds and
   c) optionally one or more other copolymerizable monomers and subsequent at least partial hydrolysis of the ester functions of the original monomers a).

2. The method as claimed in claim 1, wherein the polymers are obtained by free-radical polymerization of
   a) at least one vinyl ester of $C_1$–$C_{24}$-carboxylic acids in the presence of b) polyether-containing compounds of the formula I $$R^1-(O-(R^2-O)_u-(R^3-O)_v-(R^4-O)_w-[A-(R^2-O)_x-(R^3-O)_y-(R^4-O)_z]_s-R^5)_n \quad \text{I}$$

in which the variables independently of one another have the following meanings:

$R^1$ is hydrogen, $C_1$–$C_{24}$-alkyl, $R^6$—C(=O)—, $R^6$—NH—C(=O)—, polyalcohol radical;

$R^5$ is hydrogen, $C_1$–$C_{24}$-alkyl, $R^6$—C(=O)—, $R^6$—NH—C(=O)—;

$R^2$ to $R^4$ are —(CH$_2$)$_2$—, —(CH$_2$)$_3$—, —(CH$_2$)$_4$—, —CH$_2$—CH($R^6$)—, —CH$_2$—CHOR$^7$—CH$_2$—;

$R^6$ is $C_1$–$C_{24}$-alkyl;

$R^7$ is hydrogen, $C_1$–$C_{24}$-alkyl, $R^6$—C(=O)—, $R^6$—NH—C(=O)—;

A is —C(=O)—O, —C(=O)—B—C(=O)—O, —C(=O)—NH—B—NH—C(=O)—O;

B is —(CH$_2$)$_t$—, arylene, optionally substituted;

n is from 1 to 1000;
s is from 0 to 1000;
t is from 1 to 12;
u is from 1 to 5000;
v is from 0 to 5000;
w is from 0 to 5000;
x is from 0 to 5000;
y is from 0 to 5000;
z is from 0 to 5000; and c) optionally one or more other copolymerizable monomers and subsequent at least partial hydrolysis of the ester functions of the original monomers a).

3. The method as claimed in claim 2, wherein the polymers are obtained by free-radical polymerization of a) at least one vinyl ester of $C_1$–$C_{24}$-carboxylic acids in the presence of b) polyether-containing compounds of the formula I having an average molecular weight of from 300 to 100000 (number average), in which the variables independently of one another have the following meanings:

$R^1$ is hydrogen, $C_1$–$C_{12}$-alkyl, $R^6$—C(=O)—, $R^6$—NH—C(=O)—, polyalcohol radical;

$R^5$ is hydrogen, $C_1$–$C_{12}$-alkyl, $R^6$—C(=O)—, $R^6$—NH—C(=O)—;

$R^2$ to $R^4$ are —(CH$_2$)$_2$—, —(CH$_2$)$_3$—, —(CH$_2$)$_4$—, —CH$_2$—CH($R^6$)—, —CH$_2$—CHOR$^7$—CH$_2$—;

$R^6$ is $C_1$–$C_{12}$-alkyl;

$R^7$ is hydrogen, $C_1$–$C_{12}$-alkyl, $R^6$—C(=O)—, $R^6$—NH—C(=O)—;

n is from 1 to 8;
s is 0;
u is from 2 to 2000;
v is from 0 to 2000;
w is from 0 to 2000; and c) optionally one or more other copolymerizable monomers and subsequent at least partial hydrolysis of the ester functions of the original monomers a).

4. The method as claimed in claim 2, wherein the polymers are obtainable by free-radical polymerizable of a) at least one vinyl ester of $C_1$–$C_{24}$-carboxylic acids in the presence of b) polyether-containing compounds of the formula I having an average molecular weight of from 500 to 50000 (number average), in which the variables independently of one another have the following meaning:

$R^1$ is hydrogen, $C_1$–$C_6$-alkyl, $R^6$—C(=O)—, $R^6$—NH—C(=O)—;

$R^5$ is hydrogen, $C_1$–$C_6$-alkyl, $R^6$—C(=O)—, $R^6$—NH—C(=O)—;

$R^2$ to $R^4$ are —(CH$_2$)$_2$—, —(CH$_2$)$_3$—, —(CH$_2$)$_4$—, —CH$_2$—CH($R^6$)—, —CH$_2$—CHOR$^7$—CH$_2$—;

$R^6$ is $C_1$–$C_6$-alkyl;

$R^7$ is hydrogen, $C_1$–$C_6$-alkyl, $R^6$—C(=O)—, $R^6$—NH—C(=O)—;

n is 1;
s is 0;
u is from 5 to 500;
v is from 0 to 500;
w is from 0 to 500; and c) optionally at least one or more other copolymerizable monomers and subsequent at least partial hydrolysis of the ester functions of the original monomers a), in hair cosmetic formulations.

5. The method as claimed in claim 1, wherein the polymers are obtained by free-radical polymerization of a) at least one vinyl ester of $C_1$–$C_{24}$-carboxylic acids in the presence of b) polyether-containing silicone derivatives and c) optionally one or more other copolymerizable monomers and subsequent at least partial hydrolysis of the ester function of the original monomers a).

6. The method as claimed in claim 5, wherein the polymers are obtained by free-radical polymerization of a) at least one vinyl ester of $C_1$–$C_{24}$-carboxylic acids in the presence of b) polyether-containing silicone derivatives of the formula II

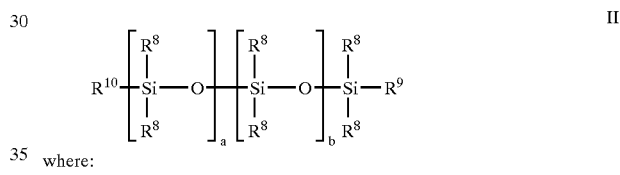

where:

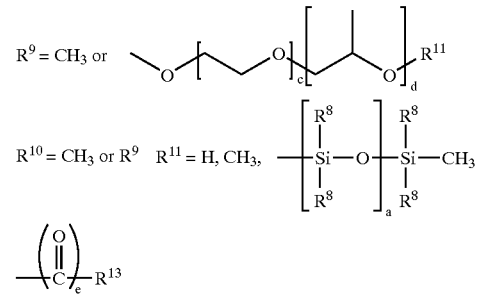

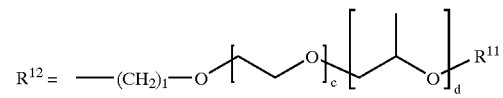

$R^{13}$ is a $C_1$–$C_{40}$ organic radical which can contain amino, carboxyl or sulfonate groups, or where e=0, is also the anion of an inorganic acid, and where the radicals $R^8$ can be identical or different, and come either from the group of aliphatic hydrocarbons having from 1 to 20 carbon atoms, are cyclic aliphatic hydrocarbons having from 3 to 20 carbon atoms, are of an aromatic nature or are identical to $R^2$, where:

with the proviso that at least one of the radicals $R^8$, $R^9$ or $R^{10}$ is a polyalkylene oxide-containing radical as defined above, and f is an integer from 1 to 6,
a and b are integers such that the molecular weight of the polysiloxane block is between 300 and 30000,
c and d can be integers between 0 and 50, with the proviso that the sum c+d is greater than 0, and e is 0 or 1, and optionally one or more other copolymerizable monomers and subsequent at least partial hydrolysis of the ester functions of the original monomers a).

7. The method as claimed in claim 6, wherein formula II has the following meaning:

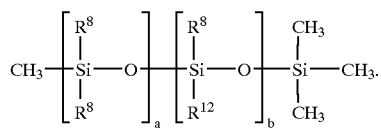

8. The method as claimed in claim 1, wherein the polymers are obtained by free-radical polymerization of
a) at least one vinyl ester of $C_1$–$C_{24}$-carboxylic acids in the presence of
b) polyether-containing compounds obtainable by reaction of polyethyleneimines with alkylene oxides and
c) optionally one or more other copolymerizable monomers and subsequent at least partial hydrolysis of the ester functions of the original monomers a).

9. The method as claimed in claim 8, wherein the alkylene oxides used are ethylene oxide, propylene oxide, butylene oxide and mixtures thereof.

10. The method as claimed in claim 8, wherein the alkylene oxide used is ethylene oxide.

11. The method as claimed in claim 8, wherein the polyethyleneimine has a molecular weight between 300 and 20000.

12. The method as claimed in claim 1, wherein the polyether-containing compounds b) have been prepared by polymerization of ethylenically unsaturated alkylene oxide-containing monomers and optionally other copolymerizable monomers.

13. The method as claimed in claim 12, wherein the polyether-containing compounds b) have been prepared by polymerization of polyalkylene oxide vinyl ethers and optionally other copolymerizable monomers.

14. The method as claimed in claim 12, wherein the polyether-containing compounds b) have been prepared by polymerization of polyalkylene oxide (meth)acrylates and optionally other copolymerizable monomers.

15. The method as claimed in claim 1, wherein c) is chosen from the group:
acrylic acid, methacrylic acid, maleic acid, fumaric acid, crotonic acid, maleic anhydride and its half-esters, methyl acrylate, methyl methacrylate, ethyl acrylate, ethyl methacrylate, n-butyl acrylate, n-butyl methacrylate, t-butyl acrylate, t-butyl methacrylate, isobutyl acrylate, isobutyl methacrylate, 2-ethylhexyl acrylate, stearyl acrylate, stearyl methacrylate, N-t-butylacrylamide, N-octylacrylamide, 2-hydroxyethyl acrylate, hydroxypropyl acrylates, 2-hydroxyethyl methacrylate, hydroxypropyl methacrylates, alkylene glycol (meth)acrylates, styrene, unsaturated sulfonic acids such as, for example, acrylamidopropane sulfonic acid, vinyl pyrrolidone, vinyl caprolactam, vinyl ethers, (e.g. methyl, ethyl, butyl or dodecyl vinyl ethers), vinylformamide, vinylmethylacetamide, vinylamine, 1-vinylimidazole, 1-vinyl-2-methylimidazole, N,N-dimethylaminomethyl methacrylate and N-[3-(dimethylamino)propyl]methacrylamide;
3-methyl-1-vinylimidazolium chloride, 3-methyl-1-vinylimidazolium methylsulfate, N,N-dimethylaminoethyl methacrylate, N-[3-(dimethylamino)propyl]methacrylamide quaternized with methyl chloride, methyl sulfate or diethyl sulfate.

16. The method as claimed in claim 1, wherein the quantitative ratios are
a) 10–90% by weight
b) 2–90% by weight
c) 0–50% by weight.

17. The method as claimed in claim 1, wherein the quantitative ratios are
a) 50–97% by weight
b) 3–50% by weight
c) 0–30% by weight.

18. The method as claimed in claim 1, wherein the quantitative ratios are
a) 60–97% by weight
b) 3–40% by weight
c) 0–20% by weight.

19. The method as claimed in claim 1, where a crosslinking is carried out after the hydrolysis.

20. The method as claimed in claim 19, where the crosslinking is carried out by aldehydes, dialdehydes or borates.

21. The method of claim 1 wherein the degree of the partial hydrolysis of the ester functions is in the range of from 1 to 100%.

22. A hair cosmetic formulation which has the following composition:
a) 0.05–20% by weight of the polymer as in claim 1
b) 20–99.95% by weight of water and/or alcohol
c) 0–79.05% by weight of other constituents.

23. A hair cosmetic formulation which has the following composition:
a) 0.1–10% by weight of the polymer as in claim 1
b) 20–99.9% by weight of water and/or alcohol
c) 0–70% by weight of a propellant
d) 0–20% by weight of other constituents.

24. A hair cosmetic formulation which has the following composition:
a) 0.1–10% by weight of the polymer as in claim 1
b) 55–94.8% by weight of water and/or alcohol
c) 5–20% by weight of a propellant
d) 0.1–5% by weight of an emulsifier
e) 0–10% by weight of other constituents.

25. A hair cosmetic formulation which has the following composition:
a) 0.1–10% by weight of the polymer as in claim 1
b) 60–99.85% by weight of water and/or alcohol
c) 0.05–10% by weight of a gel former
d) 0–20% by weight of other constituents.

26. A hair cosmetic formulation which has the following composition:
a) 0.05–10% by weight of the polymer as in claim 1,
b) 25–94.95% by weight of water
c) 5–50% by weight of surfactants
d) 0–5% by weight of another conditioning agent
e) 0–10% by weight of other cosmetic constituents.

* * * * *

UNITED STATES PATENT AND TRADEMARK OFFICE
CERTIFICATE OF CORRECTION

| | |
|---|---|
| PATENT NO. | : 6,964,774 B1 |
| APPLICATION NO. | : 09/913980 |
| DATED | : November 15, 2005 |
| INVENTOR(S) | : Dieing et al. |

It is certified that error appears in the above-identified patent and that said Letters Patent is hereby corrected as shown below:

In column 26, in claim 2, subpart (a), in formula I, at line 68:
    the letter "y" following "(R3-O)" should be written as a subscript instead of as regular text;
    the number "2" following "(R4-O)" should be written as letter --z--;
    the number "5" following "]" should be written as letter --s--.

In column 1 and 2, in formula 1, at line 17:
    all indices "u", "v", "w", "x", "y", "z" should be written as a subscript instead of as regular text;
    all index numbers "1", "2", "3", "4", "5" should be written as a superscript instead of as regular text.

Signed and Sealed this

Tenth Day of April, 2007

JON W. DUDAS
*Director of the United States Patent and Trademark Office*